(12) United States Patent
Kapil et al.

(10) Patent No.: US 6,740,490 B2
(45) Date of Patent: May 25, 2004

(54) IDENTIFICATION AND APPLICATIONS OF PORCINE REPRODUCTIVE AND RESPIRATORY SYNDROME VIRUS HOST SUSCEPTIBILITY FACTOR(S) FOR IMPROVED SWINE BREEDING

(75) Inventors: Sanjay Kapil, Manhattan, KS (US); Kumar Shanmukhappa, Manhattan, KS (US)

(73) Assignee: Kansas State University Research Foundation, Manhattan, KS (US)

( * ) Notice: Subject to any disclaimer, the term of this patent is extended or adjusted under 35 U.S.C. 154(b) by 0 days.

(21) Appl. No.: 09/772,044

(22) Filed: Jan. 29, 2001

(65) Prior Publication Data

US 2003/0165814 A1 Sep. 4, 2003

(51) Int. Cl.[7] .......................... C12Q 1/68; C12P 19/34; C07H 21/04; G01N 33/53
(52) U.S. Cl. .......................... 435/6; 435/91.2; 536/22.1
(58) Field of Search .............................. 435/6, 91.2, 7; 536/22.1

(56) References Cited

U.S. PATENT DOCUMENTS

| 6,033,844 A | | 3/2000 | Visser et al. .................... 435/5 |
| 6,143,880 A | * | 11/2000 | Soumillion et al. ....... 536/24.31 |
| 6,592,873 B1 | * | 7/2003 | Paul et al. ................ 424/218.1 |

OTHER PUBLICATIONS

Bautista, Elida M., et al., Comparison of Porcine Alveolar Macrophages and CL 2621 for the Detection of Porcine Reproductive and Respiratory Syndrome (PRRS) Virus and Anti–PRRS Antibody; *J Vet Diagn Invest* 5:163–165 (1993).
Christopher–Hennings, Jane, et al.; Detection of Porcine Reproductive and Respiratory Syndrome Virus in Boar Semen by PCR; *Journal of Clinical Microbiology* 1730–1734 (1995).
Collins, James E., et al.; Isolation of Swine Infertility and Respiratory Syndrome Virus (Isolate ATCC VR–2332) in North America and Experimental Reproduction of the Disease in Gnotobiotic Pigs; *J Vet Diagn Invest* 4:117–126 (1992).
Goyal, Sagar M.; Porcine Reproductive and Respiratory Syndrome; *J Vet Diag Invest* 5:656–664 (1993).
Kim, H.S, et al..; Enhanced Replication of Porcine Reproductive and Respiratory Syndrome (PRRS) Virus in a Homogeneous Subpopulation of MA–104 Cell Line; *Arch Virol* 133:477–483 (1993).
Wensvoort, G., et al.; Mystery Swine Disease in the Netherlands: The Isolation of Lelystad Virus; *The Veterinary Quarterly* 13:3 pp. 121–130 (1991).
Witte, Steven B., et al.; Development of a Recombinant Nucleoprotein–Based Enzyme–Linked Immunosorbent Assay for Quantification of Antibodies Against Porcine Reproductive and Respiratory Syndrome Virus; *Clin. Diagn. Lab. Immunol.* 7:4 pp. 700–702 (2000).

* cited by examiner

*Primary Examiner*—Ethan Whisenant
*Assistant Examiner*—Joyce Tung
(74) *Attorney, Agent, or Firm*—Hovey Williams LLP

(57) ABSTRACT

Porcine reproductive and respiratory syndrome virus (PRRSV) causes serious economic losses in swine. The present invention determined that CD 151 is a susceptibility factor for PRRSV infection by transfecting a cell line which is not susceptible to PRRSV infection (BHK-21) with CD 151, which rendered the cell line susceptible. Because CD 151 can be accessed in cellular material including blood platelets and germplasm, the present invention provides a non-invasive method of screening different swine for susceptibility to PRRSV, thereby improving breeding plans. In the case of a valuable animal, results from such screening can indicate any offspring's susceptibility to PPRSV. Additionally, the viral RNA-CD 151 interaction possesses high affinity and can be used as a tool to detect anti-viral compounds which can be further improved by using combinatorial chemistry. Accordingly, anti-viral compounds that can block the viral RNA-CD 151 interaction can be developed. Advantageously, transfection of CD 151 into non-simian cell lines can confer susceptibility to PRRSV and these recombinant cell lines can be used for preparation of biologics that will avoid simian cell lines which could be a source of primate viruses in xenotransplanted organs from pigs. Finally, the present invention describes the basic mechanism by which the virus RNA enters a target cell. This novel class of proteins is termed viral RNA entry proteins and a novel class of compounds named anti-RNA Entry Proteins can be used to block the entry of viral RNA, thereby preventing viral infections.

12 Claims, 9 Drawing Sheets

(1 of 9 Drawing Sheet(s) Filed in Color)

Fig. 1

```
 -31                    G TCCCGGACTC CGACGAGTGG TAGCCCCAGG
                        M  G  E  F  N  E  K  K  T  T  C  G  T  V  C  L  K
   1 ATGGGTGAGT TTAACGAGAA GAAGACAACA TGTGGCACCG TTTGCCTCAA
      Y  L  L  F  T  Y  N  C  C  F  W  L  A  G  L  A  V
  51 GTACCTGCTG TTTACCTACA ACTGCTGCTT CTGGCTGGCC GGCCTGGCTG
             M  A  V  G  I  W  T  L  A  L  K  S  D  Y  I  S
 101 TCATGGCAGT GGGCATCTGG ACGCTGGCCC TCAAGAGTGA CTACATCAGC
      L  L  A  S  G  T  Y  L  A  T  A  Y  I  L  V  V  A
 151 CTCCTGGCCT CGGGCACCTA CCTGGCCACA GCCTACATCC TGGTGGTGGC
      G  A  V  V  M  V  T  G  V  L  G  C  C  A  T  F  K
 201 GGGCGCTGTC GTCATGGTGA CCGGGGTCTT GGGCTGCTGT GCCACCTTCA
      E  R  R  N  L  L  R  L  Y  F  I  L  L  L  I  I
 251 AGGAGCGTCG GAACCTGCTG CGCCTGTACT TCATCCTGCT CCTCATCATC
      F  L  L  E  I  I  A  G  V  L  A  Y  V  Y  Y  Q  Q
 301 TTTCTGCTGG AGATCATCGC TGGTGTCCTC GCCTATGTCT ACTACCAGCA
      L  N  T  E  L  K  E  N  L  K  D  T  M  A  K  R  Y
 351 GCTGAACACA GAGCTCAAGG AGAACCTTAA GGACACCATG GCCAAGCGCT
      H  Q  P  G  H  E  A  V  T  S  A  V  D  Q  L  Q
 401 ACCACCAGCC GGGTCACGAG GCCGTGACCA GCGCTGTGGA CCAACTGCAG
      Q  E  F  H  C  C  G  S  N  N  S  Q  D  W  R  D  S
 451 CAGGAGTTCC ACTGCTGTGG CAGCAACAAC TCACAGGACT GGCGGGACAG
      E  W  I  R  L  R  E  A  R  G  R  V  V  P  D  S  C
 501 TGAGTGGATC CGCTTAAGGG AAGCCCGTGG CCGCGTGGTC CCCGATAGCT
      C  K  T  V  V  A  G  C  G  Q  R  D  H  A  F  N
 551 GCTGCAAGAC GGTGGTGGCT GGTTGTGGGC AGCGGGACCA CGCCTTCAAC
      I  Y  K  V  E  G  G  F  I  T  K  L  E  T  F  I  Q
 601 ATTTACAAGG TGGAGGGCGG CTTCATCACC AAGTTGGAGA CCTTCATCCA
      E  H  L  R  V  I  G  A  V  G  T  G  I  A  C  V  Q
 651 GGAGCACCTC AGGGTCATTG GGGCTGTGGG GACTGGCATT GCCTGTGTGC
      V  F  G  M  I  F  T  C  C  L  Y  R  S  L  K  L
 701 AGGTCTTTGG CATGATCTTC ACATGCTGCC TGTACAGGAG CCTCAAGCTG
      E  H  Y  *
 751 GAGCACTACT GACCCTGCCC TGGGCTTGGC CGCGGCTCTG TGCTTTGCTG
 801 CTGCTGCACC CAACTACTGA GCTGAGACCA CTGAGTACCA GGGGCTGGGC
 851 TCCCTGATGA CACCCACCCT GTGCCATCAC CATAACTTTG GGACCCCAA
 901 CCCCAGAGGC AAGCTTCAAG TGCCTTTCGC TGCACACCAA AGCCCAGCAG
 951 GGAAGTGAGG GGGGCTGGCG GGACGACGGT ATCGGGGGTG TTTTGTGGGG
1001 CTGCCTGAAC ACATTCTGCC TGGTGGTCAG ATGCAGGCTA GCCGGGGCCT
1051 TGCTGAGTAG GGCAAGGCCG AGTGTTCCCA GCAGGGGGAG AAGCCCTTCA
1101 CATCCCAGGC CCTTCAGGGA TTAGGGCTTT GCCTTGCAGC ACATGGCCC
1151 CATCCCAGTT TGAGAAGCTG AGTAAGCTCT GACCCTTGGG CCTGGGCCTC
1201 TGCCCCTCCC CACCCAGGCC TCGTCTCCCT CAGAGCCCCT GCTGTCTTCC
1251 CCACCGCAGT CACCACCACC CGAAATGCCA CATGGTCACT TGTGCACTGC
1301 CCCGTCCATG TGCCTGTGTG GGGCAGGGGC CTCCCGGTTT TGTTCACTGC
1351 TGTACCCAGA TGCCTACAAC CATCCCTGCC ACATACAGGT GCTCAATAAA
1401 CACTTGTGGG GCAGATGGAC GAAAAAAAAA AA
```

IDENTIFICATION AND APPLICATIONS OF PORCINE REPRODUCTIVE AND RESPIRATORY SYNDROME VIRUS HOST SUSCEPTIBILITY FACTOR(S) FOR IMPROVED SWINE BREEDING

SEQUENCE LISTING

A printed Sequence Listing accompanies this application, and has also been submitted with identical contents in the form of a computer-readable ASCII file on a floppy diskette and a CDROM.

BACKGROUND OF THE INVENTION

1. Field of the Invention

The present invention is directed towards the screening of different pig breeding lines by quantitative reverse-transcriptase polymerase chain reaction (RT-PCR) for CD 151. Selection of lines which are genetically low in or do not possess CD 151 produces offspring which are less susceptible or not susceptible at all to infection by porcine reproductive and respiratory syndrome virus (PRRSV). The present invention also concerns non-invasive methods for screening live pigs and swine germplasm for susceptibility to PRRSV. Additionally, the invention describes the development of cell lines for propagating high titer stocks for making killed and modified live virus vaccines in non-simian cell lines. Moreover, the invention describes a novel plasmid, useful in transforming previously non-susceptible cell lines into susceptible ones for producing the titer stocks used in vaccines. The invention also pertains to providing a tool for discovery of a novel class of anti-viral compounds that will block the interaction between CD 151 and PRRSV 3'-UTR RNA. This novel class of compounds has been termed anti-RNA Entry Proteins (anti-REPs).

2. Description of the Prior Art

Porcine reproductive and respiratory syndrome (PRRS) is a RNA virus which emerged in the late 1980's as an important viral disease of swine. PRRS is the most important swine health problem today. The origin and evolution of PRRSV is not known. Thus, it is a novel emerging virus of pigs. This disease, which has previously been referred to as "mystery swine disease", "swine infertility and respiratory syndrome", or "blue ear disease," is causing heavy losses in breeding herds of the United States and Canada. A similar disease has also appeared in much of Europe and the virus has been detected worldwide. The disease is manifested in two forms, one causing severe reproductive failure in pregnant sows, manifested in the form of premature farrowings, increased numbers of stillborn, mummified and weak-born pigs, decreased farrowing rate, and delayed return to estrus and the other producing respiratory distress in pigs evidenced by lesions that appear in the lungs of infected swine.

The reproductive form of the disease is described by Keffaber, K.K., "*Reproductive Failure of Unknown Etiology*", American Association of Swine Practitioners Newsletter, 1:109 (1989). The most prominent clinical symptoms of the reproductive form of the disease are spontaneous late-term abortions, premature births (which can be as high as 20–30% of all births) and the farrowing of mummified fetuses, stillborn or sickly piglets. Such clinical symptoms will typically be observed in a herd from 4–16 weeks, or even longer. Stillborn fetuses in affected litters often are in the early stages of mummification, as evidenced by tan-brown discoloration of the skin and post-mortem autolysis. Dome-shaped malformations of fetal skulls is also sometimes seen. The infection of sows may go unnoticed, or may manifest itself by an impaired general condition lasting up to a few days. For example, the sows may go off feed, and experience body temperatures either above or below normal. In the farrowing phase, the sows may exhibit depression, lethargy, pyrexia and occasional vomiting. In some affected herds, up to 75% of all piglets may be lost. The economic consequences of the disease, accordingly, are devastating.

The respiratory form of the disease exhibits clinical signs which are most pronounced in piglets of 3–8 weeks in age, but are reported to occur in pigs of all ages in infected herds. The diseased piglets grow slowly, have roughened hair coats, respiratory distress ("thumping") and increased mortality (up to about 80% pre-weaning mortality). To combat the problems associated with infection by PRRSV, vaccines have been developed in an attempt to confer immunity to the current PRRSV strains. The present vaccines are only marginally effective and are all produced in cell lines of simian origin which possessed a risk of continuous introduction of primate viruses in swine populations. Findings in preliminary studies of gross and microscopic lesions of piglets affected with the respiratory form of the disease suggest that microscopic lung lesions are an important clinical feature of this disease.

PRRSV belongs within the order Nidovirales in the family Arteriviridae. Other members in the family include equine arteritis virus, lactate dehydrogenase elevating virus, and simian hemorrhagic fever virus. Currently, there is no known human arterivirus. The PRRSV genome is a positive sense RNA about 15.1 kb in length. Untranslated regions (UTR's) of 156–220 nucleotides at the 5' end and 59–117 nucleotides at the 3' end flank the viral genome. The viral genome has eight overlapping open reading frames encoding functional and structural proteins. PRRSV grows primarily in the macrophages of infected pigs. In cell culture, the virus is known to grow in CL 2621, MA-104, MARC cell lines and in primary cultures of porcine alveolar macrophages. All of these continuous cell lines are of simian origin and pose a risk of introduction of primate viruses into swine populations. Entry of the virus occurs by receptor-mediated endocytosis and the receptor has been characterized as a heparin-like molecule. However, the mechanisms of how viral RNAs enter after endocytosis into the cell cytoplasm are not known.

Replication of arteriviruses is similar to that of the coronaviruses. Genomic and subgenomic (−) sense mRNAs are formed in the infected cells along with the (+) sense mRNAs. Subgenomic (−) sense mRNAs have been shown to function as the principal templates for mRNA synthesis in coronaviruses. Discontinuous transcription occurs in arteriviruses with the formation of a functionally monocistronic, 3'-coterminal, nested set of mRNAs. The common leader is joined to the coding region by consensus intergenic sequences through the junction sequence UCAACC. In mouse hepatitis virus (MHV), a corona virus, interaction of the leader, intergenic sequence and the body of the RNA involves cis and trans acting elements. The 3'UTR's of MHV, coxsackie-, rhino- and polioviruses were shown to be essential for the transcription of the genome. There is little sequence complementarity between the 3'UTR and upstream regulatory sequences for interaction, therefore it may be mediated through RNA-protein-RNA interactions involving the viral or cellular proteins.

There are numerous studies on the interactions of viral and cellular proteins with 5' and 3' UTR's of viruses. Sindbis virus, brome mosaic virus, QB phage and polioviruses require the interaction of certain host cell proteins with viral UTR's for transcription to proceed. Although numerous proteins have been shown to bind to these regulatory regions, only a few of them have been characterized. La protein, poly (rC) binding protein 2, and polypyrimidine tract binding protein are shown to bind to UTR's of poliovirus. Polypyrimidine tract binding protein and heterogeneous nuclear ribonucleoprotein have been shown to bind to the leader sequence of MHV. These proteins are predicted to play a role in mRNA splicing and transportation. Some cytoskeletal and chaperone proteins, like actin, tubulin, and heat shock proteins, are shown to have RNA binding activity. These proteins might play a structural role in viral RNA synthesis or in orienting and transporting the RNA replication complexes to the site of replication.

The study of host cell proteins that interact with viral RNAs is still in the infancy stage and there is a lack of important information regarding this interaction, especially with respect to host-susceptibility factors. Even in arteriviruses, such as PRRSV, the host susceptibility factors have not been studied. Thus, the markers for swine breeding for increased host susceptibility to PRRSV are not known. However, it is known that different breeds of pigs do differ in PRRSV susceptibility based on experimental infection followed by sacrificing the animals followed by further examination with histopathology and immunohistochemistry for interstitial pneumonia and presence of PRRSV antigen in the lungs.

Moreover, only simian cell lines provide the cell culture for current PRRSV vaccines which is a dangerous activity. The use of simian cell lines for these cell cultures might accidentally introduce primate viruses of significance into swine lines intended for xenotransplant purposes. Because swine are being increasingly explored as a source of xenotransplanted organs to meet the shortage of organ transplants for humans, the introduction of primate cell lines to swine populations may ultimately pose a risk to humans having xenotransplanted organs. Thus it would be prudent to avoid the use of simian cell lines in swine vaccine preparations.

Accordingly, what is needed in the art is a method of screening swine for susceptibility to PRRSV infection. Preferably, this screening should be non-invasive and able to be performed on a number of different animal fluids and cellular material, including swine germplasm and whole blood. Additionally what is needed is a method of using these screening results in a breeding program designed to lessen the susceptibility of offspring to PRRSV infection. What is further needed is a non-simian cell line for propagating high-titer PRRSV vaccine stock to avoid crossover of primate viruses into the swine population. Such a cell line will be especially adapted for vaccines used with xenotransplanted swine. Finally, what is needed is a class of compounds which can block the entry of viral RNA into cells.

SUMMARY OF THE INVENTION

The present invention solves the prior art problems mentioned above and provides a distinct advance in the state of the art. In particular, through the present invention, methods are provided which allow non-invasive genetic testing for PRRSV susceptibility, selection of swine for further breeding, the development of high-titer vaccines in non-simian cell lines, the development of compounds which can be used for PRRSV treatment, and the detection and characterization of the interaction between the 3'UTR RNA of the PRRS genome and susceptible cell lines, thereby leading to the development of novel anti-viral compounds called anti-RNA Entry Compounds.

Accordingly, one aspect of the present invention provides a method of screening swine using relatively non-invasive methods. For example, a blood sample could be drawn and the presence of CD 151 in platelets could be detected using quantitative reverse transcriptase-polymerase chain reaction (RT-PCR). The knowledge gained from this type of screen could greatly improve swine breeding plans as swine with low levels or even no detectible CD 151 could be selected for further breeding. One example of a swine breeding program which utilizes advantages of the present invention compares the CD 151 levels of an individual swine to a known standard of CD 151. This known standard is generally found by comparing the CD 151 levels from a large number of samples of cellular material (e.g. fluid or tissue) from swine and represents the average level of CD 151 detected in the samples. As different cellular materials from the same animal may have different levels of CD 151, it is preferable to compare CD 151 levels from a cellular material of known origin (blood, blood platelets, sperm cells, germplasm, semen, ova, etc.) with the known standard for that specific cellular material. Moreover, as the known standard represents an average CD 151 level for swine, an individual swine may be selected for further breeding based on their detected CD 151 level in comparison with the average. Generally, it is preferable to select swine with CD 151 levels which are lower than average as this would tend to produce offspring with increased resistance to PRRSV infection. In this manner, swine having certain levels of CD 151 which place the swine into a particular desired percentile for CD 151 levels and which retain other desirable breeding characteristics would be selected for this further breeding. Preferably, these swine would rank in the lower 50th percentile for CD 151 levels. More preferably, these swine would rank in the lower 80th percentile for CD 151 levels, still more preferably, these swine would rank in the lower 90th percentile for CD 151 levels, and most preferably, these swine would rank in the lower 95th percentile for CD 151 levels. In other words, for this most preferred grouping, 95% of all swine would have higher CD 151 levels than the individual swine being tested. Of course, CD 151 deficient swine could be further bred to produce a "knockout" line of swine which would be resistant to PRRSV infection.

In a related aspect of the present invention, cellular material in the form of germplasm such as sperm cells, or extended porcine semen could be screened for the presence of CD 151 prior to distribution to breeding facilities. Again, using the same general procedures described above, the knowledge gained from such a screen would be invaluable to future breeding plans and use of large amounts of germplasm. The ejaculation volume in swine is approximately 500 mL and the semen gets further extended so even if the animal is no longer on the farm or has died, or has been sold, the germplasm from a valuable boar can be used for many years and for many sows and could provide several future generations of piglets of desirable genotype or genetic makeup. Such frozen germplasm can also be screened for CD 151 levels and PRRSV susceptibility before artificial insemination. This screening could also indicate the susceptibility of animals or their offspring to infection by PRRSV as higher levels of CD 151 are correlated with higher virus production and release by cells. Thus, these tests will also be applicable for screening live animals on farms for their susceptibility to PRRSV. The selection of swine for further breeding based on CD 151 levels detected in germplasm would proceed as follows. A sample of germplasm would be taken and the amount or level of CD 151 in that sample would be determined by RT-PCR. This result (the amount of CD 151) would be compared with known standards for that sample as different types of germplasm would typically contain different amounts of CD 151. The known standards would be determined by the average of the quantitation of a large number of such samples. Swine exhibiting reduced levels of CD 151 in comparison to the standards (and thereby having a reduced susceptibility to PRRSV infection) yet still possessing other valuable breeding traits would be selected for further breeding. Preferably, these swine would have CD 151 levels lower than about 50% of all swine tested. More preferably, these levels will be lower than at least about 80%, still more preferably, at least about 90%, and still more preferably, at least about 95% of all swine tested. In other words, the CD 151 levels in the samples from these swine would be ranked approximately in the bottom 20%, 10%, or 5% of all swine tested. Of course, many variations of this breeding plan could result using the methods of the present invention and these variations are presumed covered provided that the level of CD 151 in a sample of cellular material is determined and this level of CD 151 influences the breeding strategy.

The present invention also provides a method of ascertaining the susceptibility to PRRS infection in animals. Such a method would include the steps of obtaining a sample of cellular material such as tissue or fluid, performing a CD 151 assay on this sample, and using the results of this assay as a measure of the animal's susceptibility to PRRS infection. The cellular material chosen for the assay can be any cellular material including any fluid or tissue or semi-purified or purified cellular preparation which contains detectible levels of CD 151. For example, blood, blood platelets, germplasm, sperm cells, ova, and semen all contain detectible levels of CD 151. One preferred assay would include the steps of extracting the RNA from the sample and then performing RT-PCR on the extracted RNA. Preferably, the results would provide a quantified amount of detected CD 151. This quantified amount (or level) could then be compared to a known standard for CD 151 levels, thereby indicating the susceptibility to PRRS infection for the animal. Still more preferably, the cellular material sample would be derived from a known origin and the known standard would represent the known standard for cellular material of the same origin.

The present invention further provides a method for determining if an animal is resistant to PRRSV infection based on the presence or absence of CD 151 in cellular material. If CD 151 is absent, the animals will typically be immune to PRRSV infection. If CD 151 is present the animals will typically be susceptible to PRRSV infection to varying degrees based on the actual CD 151 levels. In this manner, PRRSV infection resistance in animals can be classified based on the detected level of CD 151 in any sample of cellular material. Such a method would include the steps of obtaining a sample of cellular material from the tested animal, performing an assay on the sample to find the CD 151 level of that sample, comparing the CD 151 level of the tested animal with a known scale of CD 151 levels wherein the known scale corresponds to a specific degree of PRRSV infection resistance, and finally classifying the tested animal's PRRSV infection based on the comparison with the known scale. Preferably, the sample of cellular material will be of a known origin and the CD 151 scale will represent the scale for cellular material from the same origin in other animals. Such a classification may result in a percentile ranking of PRRSV infection resistance in the animal.

In another aspect of the present invention, in vitro diagnostic tests for detection of the wild type virus as well as antibodies to the virus are developed. Such test generally include the steps of obtaining a sample of cellular material from an animal, performing a diagnostic test designed to detect either the antibodies to the virus or the virus itself in a recombinant cell line, and using the results of the testing to confirm the diagnosis of PRRS in an individual swine or in a swine herd. Preferred diagnostic tests include virus isolation assays and immunodiagnostic assays such as ELISA, indirect fluorescent antibody tests, and indirect immunoperoxidase tests. Preferably, the recombinant cell line used will permit greater replication of the virus making the test more sensitive to PRRSV infection or antibody presence.

In another aspect of the present invention, higher titer PRRSV vaccines could be developed in CD 151 transformed cell lines to aid in the immunization of swine herds. In a related aspect of the present invention, other non-simian cell lines can be transformed with CD 151 and used to propagate high titer PRRSV vaccine stocks. This has become more of an issue as xenotransplantation (especially in swine) becomes more developed. Use of vaccines made in simian cells may transmit the simian viruses to swine, and hence, organs used for xenotransplantation may also be susceptible to some of these primate viruses. Thus, it will be much safer to avoid using the primate or monkey-kidney cell lines for PRRS vaccines and thereby eliminate the risk of subsequent primate virus introduction into the human transplant recipient population. For cell lines which are already susceptible to PRRS infection, transformation resulting in even higher production of CD 151 can be accomplished using methods of the present invention.

Another related aspect of the present invention will be that the high titer vaccines propagated in non-simian cell lines can be used for other applications such as development of diagnostic tests for detection of antibodies against PRRS, such as an ELISA assay.

Another related aspect of the present invention is the development and use of a plasmid or vector capable of transforming cell lines and enhancing their susceptibility to PRRSV infection. A particularly preferred plasmid in this respect has been given the designation pKSU (Genbank Accession Number AF 275666), and contains the sequence which is provided herein as SEQ ID NO. 1 and is also described in FIG. 1. Preferably, sequences having at least about 91% sequence homology or 93% sequence identity with SEQ ID NO. 1 are embraced by the present invention, whether the sequence appears as an isolated sequence, in a plasmid, or in another suitable vector. More preferably, such sequences will have at least about 95% sequence homology or 97% sequence identity and still more preferably at least about 98% sequence homology or 99% sequence identity with SEQ ID NO. 1. It is believed that this sequence represents the first reported isolated simian CD 151 sequence. Of course, the corresponding amino acid sequences for this and similar sequences are also presumed covered by the present invention as their determination requires no more than routine skill in the art.

Similarly, the present invention provides a method for incorporating CD 151 coding sequences directly in the genome of an animal. This method generally includes the step of integrating the sequence of interest (e.g. CD 151) into the chromosome using a vector designed for such an insertion. In other words, the sequence of interest is incorporated into a retro-viral vector and this retro-viral vector is used to integrate the sequence directly into a chromosome in the genome.

Accordingly, methods for preparing PRRSV vaccine stock are provided by the present invention. In general, to prepare PRRSV vaccine stock, a cell line is provided and then transformed with CD 151. This cell line can be resistant to PRRSV infection, or can be susceptible to PRRSV infection prior to transformation. The resultant transformed cell line is then infected with PRRSV and caused to produce PRRSV progeny for use in the vaccine stock. As noted above, the cell line is preferably of non-simian origin. In this manner, cell lines which are previously not susceptible to PRRSV infection are rendered susceptible after transformation with CD 151 and cell lines which were previously susceptible to PRRSV infection produce much greater numbers of progeny virus. Preferably, the transforming step includes stable transfection with a plasmid containing a CD 151 DNA sequence. The CD 151 sequence can be derived from any animal which has CD 151. Preferably the CD 151 is porcine or simian CD 151. More preferably, the CD 151 DNA sequence has at least about 91% sequence homology with SEQ ID NO. 1. Still more preferably, the CD 151 DNA sequence has at least about 95% and still more preferably at least about 98% sequence homology with SEQ ID NO. 1. The resultant vaccine stock is of higher titer than was previously obtainable prior to transformation. In some cases, this vaccine stock's titer is about 100 fold higher than was previously possible.

In another aspect of the present invention, polymorphisms in CD 151 sequences are detected and identified using RT-PCR followed by sequencing or a specifically designed test. These different polymorphisms are then analyzed to determine their effects on PRRSV susceptibility. Moreover, the level of CD 151 may be affected by regulatory sequences, such as promoters of the gene. The regulatory sequences are then analyzed to know tissue specific differences and differences among individual piglets.

Still another aspect of the present invention is the development and use of anti-REPs by the Northwestern strategy. Anti-REPs will be an important addition to the arsenal of drugs against emerging viruses. It is now believed that novel emerging viruses will all be RNA and most likely will emerge in wildlife populations due to encroachment of humans to wildlife habitats. These anti-REPs are extremely useful because they provide a readily available strategy that can be used for viral diseases that may emerge in animals (both domesticated and wild) and humans in future. It is important to understand the identification and mechanisms of RNA-binding proteins such as CD 151 for PRRSV and discovery of the compounds belonging to the category of anti-REPs. One potential method for blocking the entry of PRRSV into cells includes the step of blocking PRRSV viral RNA from interaction with CD 151. This blocking is preferably accomplished by contacting the cells with an anti-viral compound, preferably an anti-REP compound. These anti-viral compounds will be designed to occupy binding sites on CD 151, thereby blocking this viral RNA-CD 151 interaction. Preferably, these anti-viral compounds will have a greater affinity as well as a greater avidity for these binding sites than the PRRSV viral-RNA and should be producible in a high throughput manner.

Another aspect of the present invention is the ability of CD 151 to bind to RNA and this is the first report of a tetraspan molecule having RNA-binding activity. This discovery can be used to develop a novel class of compounds that prevents PRRSV or viral RNA-binding to this tetraspan and thus being released into the cell cytosol from the endosome. Combinatorial chemistry and screening by a high throughput screening system can be used to find lead compounds to treat PRRSV and potent anti-REP compounds can be found by a modified Northwestern assay.

PRRSV is a positive sense RNA virus causing serious economic losses in swine. Previous studies have shown that 3'UTR RNA of the arteriviruses plays an important role in the replication of the virus through the interaction with the cellular proteins. A cDNA library of MARC cells was constructed in the $\lambda$ ZAP Express vector and the library was screened with positive sense 3'UTR ($[\alpha\text{-}^{32}P]$ UTP) RNA of PRRSV. A RNA binding clone with an insert of 1.4 kb was found, and, after sequencing, it exhibited homology to CD 151, a transmembrane protein belonging to the tetraspan family of proteins. The MARC and BHK-21 cells were transfected with the CD 151 plasmid, and the fusion protein was immunoprecipitated with anti-Lac Z and anti-CD 151 antibodies. On Northwestern blotting, the precipitated 29 kD protein interacted with the radiolabelled 3'UTR. The precise function of CD 151 is not known, but it has been shown to play roles in cell-cell adhesion, regulation of vascular permeability, and transmembrane signaling. The BHK-21 cell line lacks CD 151 and is not susceptible to PRRSV infection, but when the BHK-21 cell line was transfected with the CD 151 plasmid, it became susceptible to PRRSV infection. Similarly, the non-simian cell lines can be transformed with CD 151 and used for PRRSV propigation to high titer.

In order to identify cellular proteins that bind to 3'UTR of PRRS virus, RNA ligand screening of a MARC cell expression library was performed. Moreover, this is the first report of the RNA binding property of a tetraspan molecule, Platelet Endothelial Tetraspan Antigen-3 (PETA-3), also designated as CD 151, and its role in PRRS virus infection. It is known that viruses bind to receptors (protein-protein interaction) and get into the cell in endosome. Under low pH conditions, the virus undergoes structural disorganization and releases viral RNA into the endosome. However, the entry of viral RNA in endosome into cell cytoplasm is not known. The present invention demonstrates that RNA binding proteins, such as CD 151, help PRRSV to enter into cell cytoplasm for further replication of the virus (FIG. 9).

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIG. 1 is the nucleotide sequence (SEQ ID No: 1) of the simian CD 151 cDNA clone, and the predicted amino acid sequence wherein the putative transmembrane domains are underlined and the inframe stop codon is indicated by an asterisk;

DETAILED DESCRIPTION OF THE PREFERRED EMBODIMENT

Figure 2:
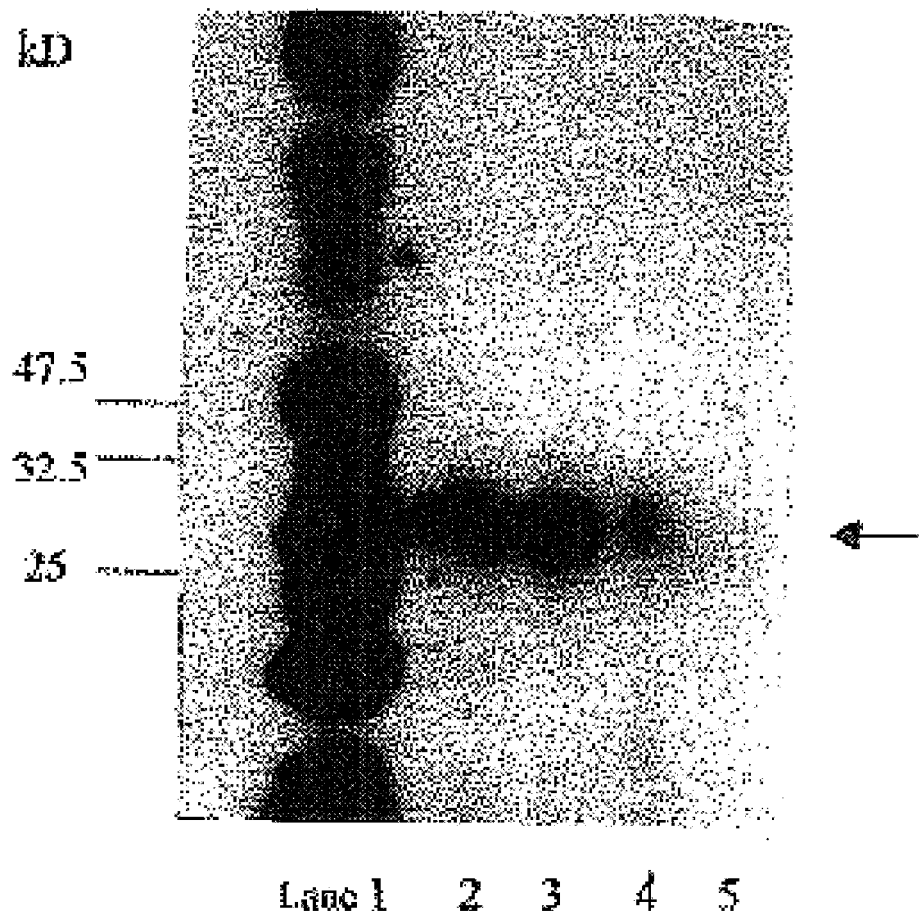
FIG. 2 is a photograph of the RNA-binding activity of the CD 151 protein detected by immunoprecipitation with CD 151 mAb in a Northwestern blotting assay.

The following examples set forth preferred embodiments of the present invention. It is to be understood, however, that these examples are provided by way of illustration and nothing therein should be taken as a limitation upon the overall scope of the invention.

As used herein, the following definitions will apply: "Sequence Identity" as it is known in the art refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403–410 (1990). The BLASTX program is publicly available from NCBI and other sources (BLAST Manual, Altschul, S. et al., NCVI NLM NIH Bethesda, Md. 20894, Altschul, S. F. et al., J. Molec. Biol., 215:403–410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 95% "sequence identity" to a reference nucleotide sequence, it is intended that the nucleotide sequence of the given polynucleotide is identical to the reference sequence except that the given polynucleotide sequence may include up to 5 point mutations per each 100 nucleotides of the reference nucleotide sequence. In other words, in a polynucleotide having a nucleotide sequence having at least 95% identity relative to the reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 95% sequence identity to a reference amino acid sequence, it is intended that the given amino acid sequence of the polypeptide is identical to the reference sequence except that the given polypeptide sequence may include up to 5 amino acid alterations per each 100 amino acids of the reference amino acid sequence. In other words, to obtain a given polypeptide sequence having at least 95% sequence identity with a reference amino acid sequence, up to 5% of the amino acid residues in the reference sequence maybe deleted or substituted with another amino acid, or a number of amino acids up to 5% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

Similarly, "sequence homology", as used herein, also refers to a method of determining the relatedness of two sequences. To determine sequence homology, two or more sequences are optimally aligned as described above, and gaps are introduced if necessary. However, in contrast to "sequence identity", conservative amino acid substitutions are counted as a match when determining sequence homology. In other words, to obtain a polypeptide or polynucleotide having 95% sequence homology with a reference sequence, 95% of the amino acid residues or nucleotides in the reference sequence must match or comprise a conservative substitution with another amino acid or nucleotide, or a number of amino acids or nucleotides up to 5% of the total amino acid residues or nucleotides, not including conservative substitutions, in the reference sequence may be inserted into the reference sequence.

A "conservative substitution" refers to the substitution of an amino acid residue or nucleotide with another amino acid residue or nucleotide having similar characteristics or properties including size, hydrophobicity, etc., such that the overall functionality does not change significantly.

Isolated" means altered "by the hand of man" from its natural state., i.e., if it occurs in nature, it has been changed or removed from its original environment, or both. For example, a polynucleotide or polypeptide naturally present in a living organism is not "isolated," but the same polynucleotide or polypeptide separated from the coexisting materials of its natural state is "isolated", as the term is employed herein.

"Cellular material" refers to cells, tissues, and fluids containing material of cellular origin.

"Anti RNA Entry Proteins" or Anti REPs" refer to a novel class of chemicals or chemical analogues that prevent binding of the viral RNA, with an RNA protein. These Anti REPs are nontoxic to mammalian cells but are able to prevent infection of cells from RNA viruses.

EXAMPLE 1

This example identifies and describes the cells, virus and monoclonal antibodies used in later experiments, prepares the λ Zap expression library, details the cloning and probe preparation of the 3'UTR of the PRRSV genome, describes the screening of the cDNA library for cells containing CD 151, describes the transfection of cells with plasmid containing CD 151, and verifies that the transfection was successful and that CD 151 binds to the 3'UTR of PRRS virus.

Materials and Methods

The MARC, COS-7, Vero, CL2621, MA-104 (derivatives of African green monkey kidney cells) and BHK-21 (Baby hamster kidney) cell lines were used in the study. The MARC cells were grown in Eagle's minimum essential medium (MEM) (Life Technologies, Inc., Gaithersburg, Md.) supplemented with 10% fetal calf serum (FCS; Hyclone, Logan, Utah). Dulbecco's minimum essential medium (Life Technologies, Inc., Gaithersburg, Md.) with 10% FCS was used to cultivate BHK-21 cells. The ATCC VR 2332 strain of PRRS virus was used in the study. Unless otherwise stated, the virus was propagated in MARC cells. The anti-CD 151 monoclonal antibody (MAb) clone 14A2.H1 was purchased from Pharmingen International, San Diego, Calif. The anti-β-galactosidase MAb clone D19-2F3-2 (Boehringer Mannheim, Indianapolis, Ind.) and the anti-PRRSV nucleoprotein MAb, SR 30 (Rural Technologies, Brookings, S. Dak.), were used in the study.

To prepare the λ Zap expression library, the MARC cell line cDNA library was prepared using a ZAP Express cDNA synthesis kit (Stratagene, La Jolla, Calif.) following the manufacturer's instructions. Total cellular RNA was extracted from the cells by the acid phenol-guanidinium isothiocyanate method. The mRNA was isolated from total cellular RNA using an oligo(dT) cellulose column (Stratagene, La Jolla, Calif.), and then 5 μg of mRNA was converted to cDNA and cloned directionally in the λ ZAP Express vector. The cDNA library was packaged using the ZAP Express cDNA Gigapack III Gold cloning kit (Stratagene, La Jolla, Calif.). The quality of the library was verified by blue/white screening and also by confirming the size of the insert.

To clone the 3'UTR of PRRSV genome and prepare a probe, the 3'UTR was cloned into the pCR II vector by RT-PCR amplification of the PRRSV RNA by TA cloning using the forward primer 5'-CCCCATTTTCCT CTAGCGACTG-3' (SEQ ID No. 2) and the reverse primer 5'-CGGCCGCATGGTTCTCGCCAAT-3' (SEQ ID No. 3). The [$\alpha$-$^{32}$P]UTP RNA transcript was prepared by in vitro transcription. The cDNA was linearized by digestion with BamHI and then transcribed in vitro using a Riboscribe™ (Epicentre Technologies, Madison, Wis.) T7 RNA synthesis kit and following the manufacturer's instructions. The DNA template was digested with 1 MBU of RNase-free DNase for 15 minutes at 37° C. Quick Spin™ columns (Boehringer Mannheim, Indianapolis, Ind.) were used to remove free nucleotides. The probe was precipitated using 0.3 M sodium acetate and 2.5 volumes of 100% ethanol at −20° C. for 30 minutes. The activity of the probe was measured with a radioactive counter (Bioscane, Inc., Washington, D.C.).

Next, the cDNA library was screened by Northwestern blotting as previously described with slight modifications. In all the rounds of screening, plaques were induced for 1.5 hours during the first lift and 2 hours for the second with 10 mM IPTG. Nitrocellulose membranes from plaque lifts were denatured in 6 M guanidinium hydrochloride for 30 minutes and gradually renatured with equal changes of single binding buffer (SB Buffer: 15 mM HEPES [pH 7.9]; 50 mM KCl, 0.01% [v/v] Nonidet P-40; 0.1% [w/v] Ficoll 400-DL; 0.1% [w/v] PVP-40; 0.1 mM $MnCl_2$, 0.1 mM $ZnCl_2$; 0.1 mM EDTA; 0.5 mM DTT) every 10 minutes. During prehybridization and hybridization 250 μl of ssDNA and 5 μl (10 mg/ml) of yeast tRNA were added to 5 ml of SB buffer to block non-specific binding. Hybridization was performed overnight with the 3' UTR PRRSV [$^{32}$P]RNA probe at 500,000 cpm/ml. RNA binding activity was detected by autoradiography.

The corresponding positive plaques were cored and eluted in 1 ml of SM buffer with 40 μl chloroform. The inserts were excised using the Gigapack III gold cloning kit. The insert, now in the pBK-CMV vector, was sequenced manually with T7 and T3 primers using a Sequitherm EXCEL II DNA sequencing kit (Epicentre Technologies, Madison Wis.). Sequencing was also performed at the Iowa State University Sequencing Facility in Ames, Iowa. A BLAST homology search was carried out to identify similar proteins.

To transfect the BHK-21 and MARC cell lines, pBK-CMV plasmid containing CD 151 gene using Lipofectamine reagent following manufacturer's instructions (Life Technologies, Inc., Gaithersburg, Md.) was used. For transient transfection, cells were harvested 24 hours after transfection. Stable transfection was done by G418 (Omega Scientific, Inc., Tarzana, Calif.) selection in growth medium at a concentration of 1 mg/ml for BHK-21 cells and 0.7 mg/ml for MARC cells. After selection, cells were maintained in the presence of G418 at 0.5 mg/ml for BHK-21 cells and 0.35 mg/ml for MARC cells. The expression of CD 151 was measured by immunoprecipitation.

Next, to demonstrate that CD 151 binds to the 3'UTR of PRRS virus, a Northwestern blot of the immunoprecipitated CD 151 protein was performed. Transfected cells in 24 well plates were lysed in 100 μl of single detergent lysis buffer (50 mM Tris-HCl [pH 8], 150 mM NaCl, PMSF 100 μg/ml and 1% [v/v] NP-40). To 50 μl of cell lysate, 1 μl of Mab (anti-CD 151 and anti-β-galactosidase antibodies) was added and rocked overnight at 4° C. Immunocomplexes were precipitated on ice for 2 h with addition of 4 μl of formalin-fixed *S. aureus* cells and centrifuged at 4,000×g for 10 minutes. All subsequent washes were done by centrifugation at 12,000×g for 10 minutes. The pellet was washed once in cold TSA (0.05 M Tris-HCl [pH 8.0]; 0.15 M NaCl; 0.025% $NaN_3$), 1% Triton X-100 and 1% SDS. The second wash was done in cold TSA alone followed by two washes in 10 mM Tris-HCl [pH 7.5] containing 1 mM EDTA. The pellet was suspended in 20 μl of 2× SDS loading buffer and electrophoresized on a 10% SDS-PAGE gel. The proteins were blotted on nitrocellulose membrane and the Northwestern blot was carried out as described above.

Results

In order to identify the MARC cell proteins binding to 3'UTR RNA of PRRSV, a cDNA library of MARC cells was made and screened by Northwestern blotting using radiolabelled 3'UTR. The MARC cell cDNA library had a titer of $10^8$ plaque forming units (pfu) with an average insert size of 1–4 kb (Data not shown). Approximately $6 \times 10^6$ plaques were screened by Northwestern blotting. The single reacting clone was obtained by repeated plaque purification and rescreening five times. In the last round of screening, a single isolated plaque was cored and excised. On restriction digestion, the size of the insert was found to be 1.5 kb (data not shown). After manual sequencing, a BLAST search showed that the insert had 98% homology with CD 151/PETA-3, a tetraspan molecule. Sequencing of the complete insert was also performed at the Iowa State University Sequencing Facility in Ames, Iowa. The insert was a full-length cDNA with start and stop codons and also a poly (A) tail. This is the first report of the complete sequence of a simian CD 151 gene. The sequence (Genbank accession number, AF275666) is shown in FIG. 1 with the putative transmembrane region underlined. Although the sequence provided is simian, it is believed that CD 151 sequences isolated from other animal lines (e.g. swine) could also be used due to their predicted homology with this simian CD 151 sequence. The presence of porcine CD 151 in alveolar macrophages has been proven by Western Blot (see FIG. 5).

Figure 3:
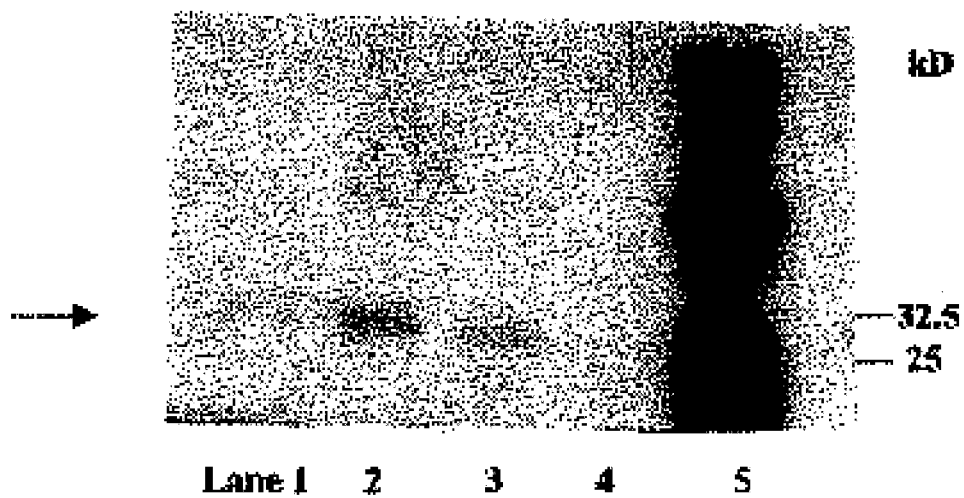
FIG. 3 is a photograph of the RNA binding activity of the CD 151 protein detected by immunoprecipitation with $\beta$-galactocidase mAb in a Northwestern blotting assay.

Immunoprecipitation followed by Northwestern blotting was carried out to validate the observation that CD 151 has RNA binding activity. Both BHK-21 and MARC cells were transfected with the pBK-CMV plasmid containing the CD 151 insert (obtained by library screening). Since CD 151 was to be expressed as a lac Z fusion protein, the transfected cell lysate was immunoprecipitated with both anti-CD 151 and anti-β-galactosidase MAbs. The protein immunoprecipitated with both MAbs exhibited RNA binding activity when probed with 3' UTR PRRSV [$^{32}$P]RNA as shown in FIGS. 2 and 3 while the controls were negative. This proves that the expressed protein, which is CD 151, has PRRSV RNA binding activity and that it binds to the 3' UTR of PRRSV. In FIG. 2, lane 1 contained the MARC lysate (without immunoprecipitation), lane 2 contained transfected MARC cells, lane 3 contained transfected BHK-21 cells, lane 4 contained untransfected MARC cells, and lane 5 contained untransfected BHK-21 cells. For FIG. 3, lane 1 contained untransfected BHK-21 cells, lane 2 contained transfected BHK-21 cells, lane 3 contained transfected MARC cells, lane 4 contained untransfected MARC cells, and lane 5 of FIG. 3 is the MARC cell lysate (without immunoprecipitation).

EXAMPLE 2

Figure 7A:
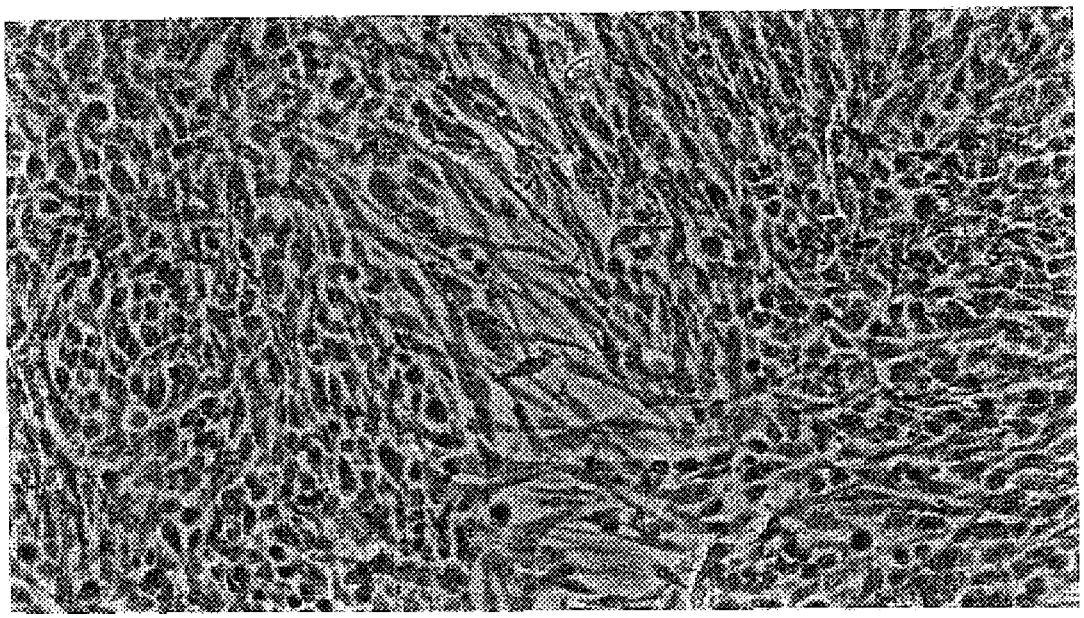
FIG. 7a is a photograph of immunohistochemistry staining to detect the presence of PRRSV in wild-type BHK-21 cells showing no detection of PRRSV antigen.
Figure 7B:
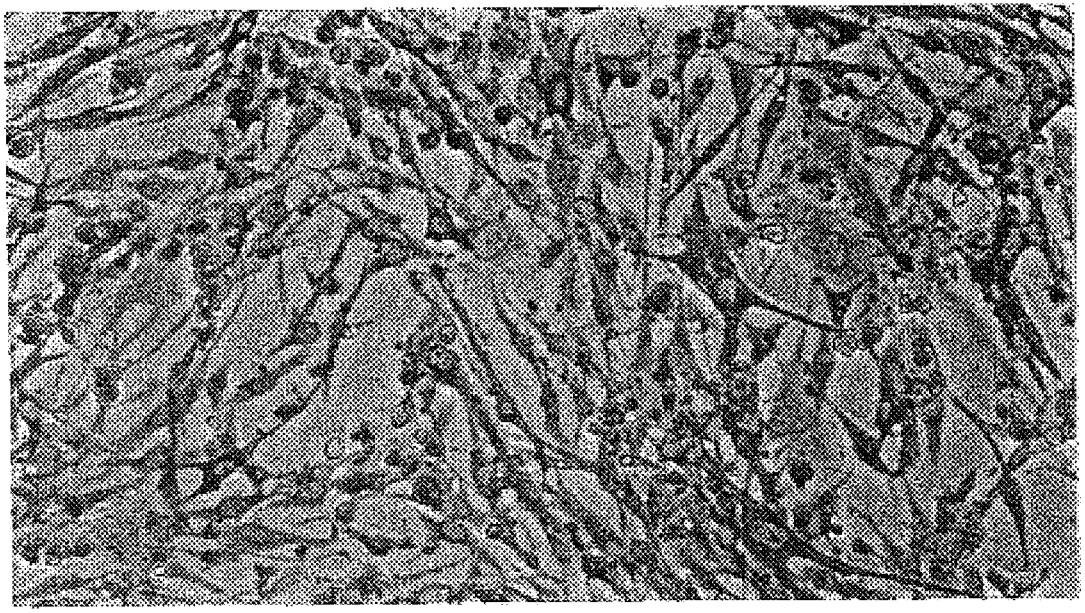
FIG. 7b is a photograph of immunohistochemistry staining to detect the presence of PRRSV in BHK-21 cells which have been transfected with CD 151.

This example determined that CD 151 expression by BHK-21 cells rendered the cells susceptible to PRRS infection.
Materials and Methods To determine whether BHK-21 cells expressing CD 151 (obtained by stable transfection) become susceptible to PRRSV infection, immunohistochemical staining was performed. Cells were seeded in 24 well plates and infected with PRRSV at a multiplicity of infection (MOI) of 0.01 at 37° C. for 1 hour. Infectivity was determined by immunohistochemistry 24-hours post infection. Cells were fixed in acetone-PBS (3:1, v/v) for 10 minutes at 4° C. and air-dried for 5 minutes. The primary antibody, anti-PRRSV nucleoprotein MAb (1:1000 dilution in PBS) was added and incubated for 1 hour at 37° C. Cells were then washed once in PBS for 10 minutes and incubated with anti-mouse IgG biotinylated antibody (Vector Labs, Burlingame, Calif.) for 30 minutes at room temperature (RT). After washing once in PBS for 10 minutes, avidin-biotin enzyme complex (Vector Labs) was added and incubated for 30 minutes at RT. The cells were then washed once in PBS for 10 minutes, once in distilled water for 5 minutes, then DAB substrate was added and incubated in the dark for 10 minutes. The cells were washed in distilled water for 5 minutes, counterstained with Gill's-1 hematoxylin for 30 seconds, washed in tap water, then examined by light microscopy.
Results The results for this example are given in FIGS. 7a and 7b. The parent BHK-21 cell line pictured in FIG. 7a was not susceptible to PRRSV but recombinant CD 151-transformed BHK-21 cells pictured in FIG. 7b were positive for the PRRSV antigen, thereby indicating susceptibility to PRRSV infection. Thus, the introduction of CD 151 rendered a previously unsusceptible simian cell line susceptible to PRRSV infection. As shown in FIG. 2, untransfected MARC cells contain CD 151 while untransfected BHK-21 do not contain CD 151. Interestingly, untransfected MARC cells are susceptible to PRRSV infection while untransfected BHK-21 cells are not.

EXAMPLE 3

Figure 8:
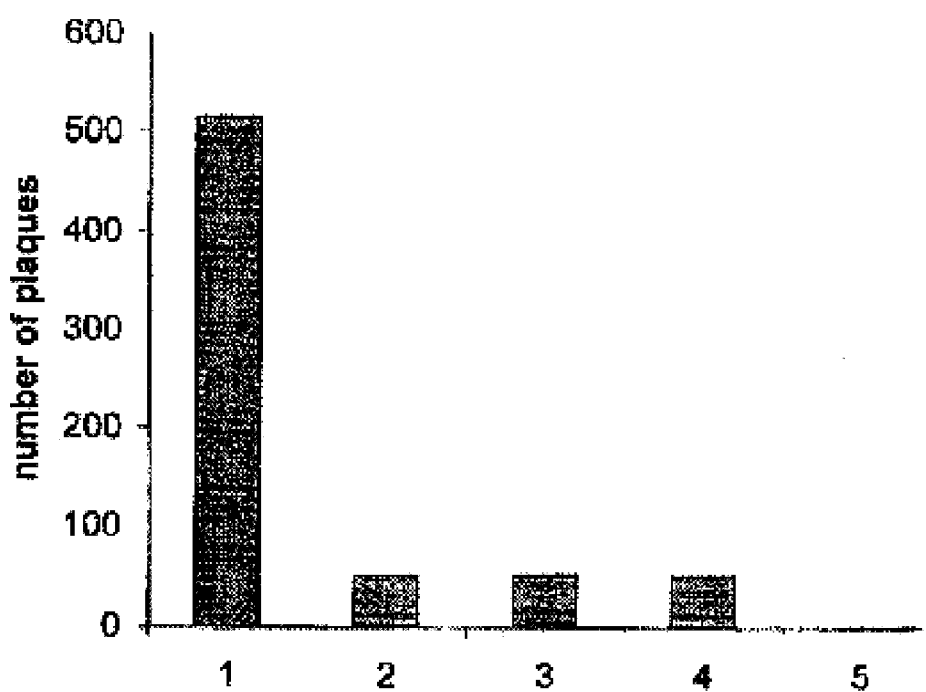
FIG. 8 is a graph illustrating the enhanced PRRSV production by MARC cells after stable transfection with CD 151.

This example utilized a virus burst assay to assess the effects of MARC cells which overexpress CD 151.
Materials and Methods The monolayer of MARC cells overexpressing CD 151 (obtained by stable transfection as described in Example 1) was infected with PRRSV at a MOI of 0.1 at 37° C. for 1 hour. Cells were washed twice in MEM and overlaid with 1 ml of MEM supplemented with 1% FCS. After incubating for 18 hours, cells were lysed by freeze thawing and cell debris was removed by centrifugation at 12,000×g for 5 minutes. The amount of virus in the supernatant was titrated by plaque assay using parent MARC cells. To determine if there are any effects of overexpression of CD 151 on PRRSV replication, MARC cells were examined with respect to the effect on infectivity level. The MARC cells (both parent and transfected progeny cell line overexpressing CD 151) were infected with equal amounts of plaque purified PRRSV and allowed to grow for one complete replication cycle (18 hours). The level of PRRSV was measured by plaque assay using parent MARC cells. In plaque assay, 100 µl of serial dilutions (10-fold) of the supernatant were used for infection as described above. After infection, the monolayer was washed once in PBS and once in MEM, then overlaid with 1 ml MEM containing 1% FCS and 1% agar. Plaques were visualized after 1 day of incubation at 37° C. by staining with 0.01% neutral red.
Results There was an approximately 100-fold increase in the amount of virus in transfected MARC cells overexpressing CD 151 as compared to parent MARC cells and these results are given in FIG. 8. When these results are taken in combination with the results from the previous experiment on viral entry, it is believed that CD 151 may have increased the levels of PRRSV infection by promoting viral RNA or viral entry. Thus, introduction of CD 151 can be used to produce higher titer stocks of PRRSV. Similarly, determining the amount or expression of CD 151 in a particular swine will give an indication as to their susceptibility to PRRS infection, in comparison to a standard. In this manner, a large number of samples from different tissues and fluids will be assayed for their CD 151 levels in order to establish an average or standard for that tissue or fluid. Individual levels of CD 151 obtained from the same tissue or fluid can then be compared to this average or standard in order to determine an individual animal's susceptibility to PRRS infection.

EXAMPLE 4

This example utilized RT-PCR to detect CD 151 mRNA in MARC cells.

Materials and Methods

RNA was extracted from the PRRSV infected MARC cells using the acid phenol-guanidinium isothiocyanate method. RNA quality was evaluated by agarose gel electrophoresis. RT-PCR was performed using the GeneAmp RNA PCR kit (Perkin Elmer, Foster City, Calif.) with forward 5'-CCTACCTGGCCACAGCCTAC-'3 (SEQ ID No. 6) and reverse 5'-ACAGGCGCAGCAGGTTCCGA-'3 (SEQ ID No. 7) primers. The reverse transcription reaction was performed at 42° C. for 45 minutes. 95° C. for 10 minutes and 5° C. for 5 minutes. PCR was done at 94° C. for 2 minutes, 94° C. for 30 sec, 55° C. for 30 sec, 72° C. for 15 sec, for 25 cycles and 72° C. for 30 minutes. The products were analyzed in 2% agarose gels stained with ethidium bromide.

Results

Figure 4:
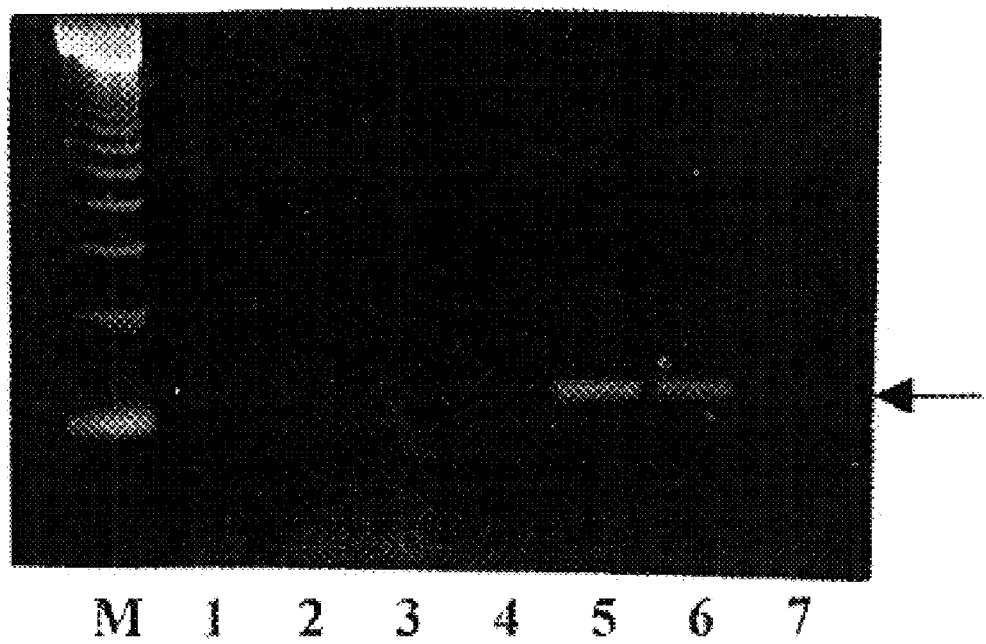
FIG. 4 is a photograph of the in vivo RNA binding activity of the CD 151 protein, as demonstrated by RT-PCR after immunoprecipitation of PRRSV infected MARC cell lysates.

A predicted RT-PCR result showing the amplification of the 149 bp amplicon is shown in FIG. 4. In this figure, the in vivo binding activity of CD 151 protein was demonstrated by RT-PCR after immunoprecipitation with CD 151 MAb of infected MARC cell lysates. In this figure, lane M is a 123 bp ladder, lane 1 is the PCR-ve control, lane 2 is the uninfected but immunoprecipitated MARC cell line, lane 3 is the infected immunoprecipitated with unrelated wasp (Cotesia folepis) MAb, lane 4 is the infected MARC cells immunoprecipitated with CD 151 MAb with no UV-crosslinking CL 2621 cell line; lane 5 is the infected MARC cells immunoprecipitated with CD 151 MAb after 15 minutes of UV crosslinking, lane 6 is the infected MARC cells immunoprecipitated with CD 151 MAb after 30 minutes of UV crosslinking, and lane 7 is the infected MARC cells immunoprecipitated with CD 151 MAb after 45 minutes of UV crosslinking.

EXAMPLE 5

This example determined if CD 151 possessed in vivo RNA binding activity by utilizing in vivo cross-linking.

Materials and Methods

MARC cell monolayers in 24 well plates were infected with PRRSV at a MOI of 0.1 at 37° C. for 1 hour. The monolayer was washed 3 times in PBS, twice in MEM, and replaced with MEM supplemented with 1% FCS. Eighteen hours post infection, the cells were washed twice in PBS then covered in fresh PBS and held on ice in a UV cross linker (Fisher Scientific, Pittsburgh, Pa.) at a distance of 10 cm from the 300 λ light source to be irradiated for 15, 30, and 45 minutes. After irradiation, the PBS was removed and the cells were lysed by addition of 50 µl of single detergent lysis buffer then freeze thawed. Immunoprecipitation was performed as described above using anti-CD 151 MAb except that IgG coupled sepharose beads were used instead of formalin-fixed S. aureus cells. Proteineous material was digested with Proteinase-K (4 µg/ml) for 15 minutes at 37° C. and RNA was extracted using the phenol-guanidinium method. RT-PCR was performed to determine the presence of PRRSV RNA using forward 5'TGGGCTGGCATTCT-TGAGGC'3 (SEQ ID No. 4) and reverse 5'TTCGGGCCGCATGGT-TCTCGC'3 (SEQ ID No. 5) primers.

Results

UV cross-linking followed by RT-PCR was performed to determine if CD 151 possesses in vivo RNA binding activity. The rationale was that if there was any interaction between the CD 151 protein and the 3' UTR RNA of PRRSV inside the cell, the complex should immunopreciptiate with the addition of anti-CD 151 MAb. The MARC cells were infected with PRRSV and to strengthen the interaction between 3' UTR RNA of PRRSV and CD 151, UV crosslinking was performed as described in the methods. Immunoprecipitated complex was treated with proteinase K to remove the proteinaceous material. The 3' UTR RNA of PRRSV was detected in the immunoprecipitate by RT-PCR as shown in FIG. 4. The interaction between the CD 151 protein and the 3' UTR of PRRSV was strong and 15 minutes of UV-induced cross-linking was sufficient to immunoprecipitate RNA along with CD 151 while the control with non-specific MAb was negative. Thus, CD 151 does possess in vivo RNA binding activity.

EXAMPLE 6

This example utilized western blotting to detect the CD 151 in MARC, BHK-21, and Vero cell proteins.

Materials and Methods

MARC, BHK-21 and VERO cell proteins were electrophoresed in 10% SDS-PAGE gel and blotted onto a nitrocellulose membrane. After blocking overnight in 5% non-fat dried milk in PBS, the membrane was incubated in anti-CD 151 MAb (1:2,000 in PBS-T) at room temperature for 5 hours. The membranes were washed in PBS-T for 15 minutes twice and incubated in anti-mouse HRPO conjugate (1:10,000) for 2 hours at room temperature. After washing, the proteins were detected by 3, 3', 5, 5'-tetra-methylbenzidine (TMB) membrane peroxidase substrate following manufacturer's instructions (Kirkegaard and Perry Laboratories, Gaithersburg, Md.).

Results

Figure 5:
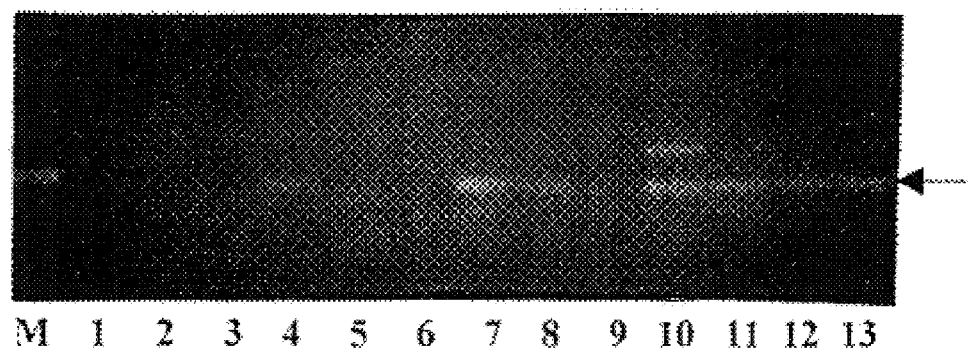
FIG. 5 is a photograph of the RT-PCR result illustrating the amplification of the CD 151 105 bp amplicon.
Figure 6:
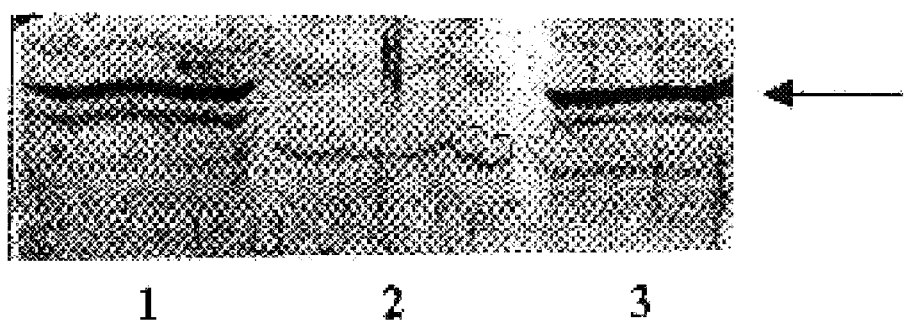
FIG. 6 is a photograph of the results of a western blotting experiment detecting the presence of CD 151.

The presence of CD 151 in susceptible cells was determined by western blotting using anti-CD 151 MAb. As shown in FIGS. 5 and 6, the susceptible MARC cells have CD 151 protein while the non-susceptible BHK-21 cells lack the protein. Moreover, transfected BHK-21 cells (FIG. 5, lane 13) do have CD 151 and are susceptible to PRRSV infection. There has been no report of susceptibility of COS-7 cells for PRRSV, while in Vero cells, the PRRSV enters the cells but does not result in productive viral infection. The Vero cells might lack other cellular factors required for PRRSV infection. These results indicate that CD 151 is one of the factors in determining the susceptibility to PRRSV infection with possible involvement of additional intracellular factors.

EXAMPLE 7

This example determined the correlation between the presence of CD 151 and susceptibility to PRRSV infection.

Materials and Methods

To determine the possible relationship between the presence of CD 151 and susceptibility of to PRRSV infection, RT-PCR using CD 151 specific primers was performed to screen susceptible and non-susceptible cell lines. These cell lines included MA 104, MARC, Vero, COS-7, the three of which are all derived from African green monkey cells, ST, BHK-21, MDBK and HRT (Human rectal tumor cells) cell lines. Total RNA was extracted as described in Example 4 and the presence of CD 151 was detected by RT-PCR using the procedures and primers described in Example 4.

Results

In MA 104, MARC 145, Vero, COS-7, and ST cell lines there was a 105 bp amplicon which was of the expected size. There were additional higher bands in CL2621, Vero, and COS-7 cell lines that could be due to the presence of alternate spliced forms of CD 151. The CD 151 was absent in BHK-21, MDBK (See FIG. 5) and HRT cell lines. Interestingly MARC 145, MA 104, and CL2621 are the cell lines susceptible to PRRSV infection while BHK-21 cell lines are non-susceptible. In the past, is was believed that the only cells that were susceptible to PRRSV were the simian cell lines CL-2621 and MARC-145 swine alveolar macrophages. Thus, the present invention refutes the previous claim that only simian cell lines are susceptible to PRRSV (see U.S. Pat. No. 5,846,805) because after transfection with CD 151, which is an accessory factor, non-simian cell lines are susceptible to PRRS virus. The BHK-21, MA 104, COS-7, ST, MDBK, and HRT18 cell lines are available from the American Type Culture Collection (ATCC), 12301 Parklawn Drive, Rockville, Md. 20852. The representative accession numbers are: BHK-21 is ATCC # CRL8544; MA104 is ATCC# CRL2378; COS-7 is ATCC# CRL1651; ST is ATCC# CRL1746; MDBK is ATCC# CCL22; and HRT18 is ATCC# CCL244. The MARC 145 cell line was obtained from National Veterinary Sciences Laboratory (NVSL) in Ames, Iowa and CL2621 is a proprietary cell line obtained from NVSL, Ames, Iowa. The Vero cell line has been accorded ATCC# CCL8 1. Thus, this example provides further evidence that CD 151 plays an important role in PRRSV infection.

EXAMPLE 8

This example determined the lack of direct protein-protein interaction between CD 151 protein and PRRSV proteins, thereby proving that CD 151 is an accessory protein but not a PRRSV viral receptor.
Materials and Methods
After establishing that CD 151 is essential for PRRSV infection, the potential for direct interaction between the PRRSV proteins and CD 151 was determined by coimmunoprecipitation. The infected MARC cells were immunoprecipitated with CD 151 MAb and the presence of PRRSV proteins in the immunoprecipitate was detected by PRRSV polyclonal antibody as the primary antibody and anti-swine HRPO as the secondary antibody followed by detection with the ECL western blot detection system (Amersham Pharmacea Biotech, Piscataway, N.J.). The coimmunoprecipitation was also performed by first immunoprecipitating with PRRSV polyclonal antibody and checking for the presence of CD 151 in the immunoprecipitate by CD 151 monoclonal antibody as the primary antibody and anti-mouse HRPO as the secondary antibody.
Results
There was no direct interaction between the CD 151 and PRRSV viral protein. This eliminates the possibility of CD 151 as a receptor. However, it does not rule out the possibility of an indirect interaction between CD 151 and PRRS viral protein. The indirect interaction will involve identification of yet another protein that could fit and complete the interaction between CD 151 and PRRS viral protein. Thus, viral RNA-protein interaction has been validated but there is no direct protein-protein interaction between CD 151 and PRRSV viral proteins. Accordingly, CD 151 is an accessory protein but not a receptor protein because it enhances PRRSV titers, and thus enhances and mediates the entry of viral RNA.

EXAMPLE 9

This example reviews the methods used to discover chemical compounds used to stop the interaction between viral RNA and CD 151 and provide for a novel class of anti-viral compounds called anti-RNA entry proteins.
Materials and Methods
Based on this invention it appears that entry of viral RNA into the cell is mediated by the interaction of the viral RNA with the RNA-binding protein. This test can be carried out easily in vitro. In a high-throughput system, the motif of the CD 151 or the full-length CD 151 can be spotted with an automatic instrument on nitrocellulose or in any solid-binding matrix. In a negative control, where no drug is present, the binding aptamer of RNA in the form of a ssDNA can be fluorescently labeled and subsequently added in a well. If no drug is present, a maximum level (100%) of fluorescence or binding activity will be observed. A wide variety of unknown chemicals can be added to the plate. The compounds that block the binding of the oligonucleotide with the RNA-binding aptamer will be further modified to find some effective non-toxic compounds that could be used to block the entry of PRRSV RNA in the cells. Similar principles can be used for the discovery of treatments for a wide variety of animal viruses. It is believed that this novel class of pharmaceuticals has not been described in the literature.

Alternatively, with the discovery of yeast hybrid systems 3' UTR RNA of PRRSV and CD 151 protein can be adapted to the yeast tri-hybrid system for discovery of compounds that will block their interaction.

EXAMPLE 10

This example shows a non-invasive method for the utilization of the present invention in screening live pigs and stored germplasm for CD 151 mRNA and levels of susceptibility of possible progeny to PRRSV. Additionally, this Example is similar to Example 4 and illustrates applications of this invention in screening live pigs boar semen and extends the application of the present invention to subsequent litters in future generations in swine breeding programs for improved swine resistance to PRRS virus.
Materials and Methods
On the basis of this invention, it is clear that the level of CD 151 is a critical factor in determination of the susceptibility of the target cell to PRRSV. Different breeding lines of pigs will be screened by quantitative RT-PCR for the level of CD 151 in cellular material such as alveolar macrophages, semen, germ cells, ova, and platelets. The lines of pigs having lower levels of CD 151 in target organs are expected to be less susceptible to PRRS and are thus less affected by the harmful effects of PRRS infection. Currently, pigs are selected on the basis of sacrificing after infection and are mated. The animals found to carry relatively less amounts of CD 151 will be selectively mated against PRRS susceptibility. This will allow a non-invasive method of checking the animals. With the help of CD 151 knockout experiments, it will be possible to develop a pig line that is completely resistant to PRRS virus infection.
Results
This example demonstrates that the present invention overcomes the current limitation of sacrificing different lines of pigs for determining their susceptibility after experimental infection with PRRSV. Using non-invasive diagnostic methods such as peripheral blood platelets, stored germplasm, or extended and non-extended porcine germplasm, swine breeding operations should be able to select for animals that have reduced susceptibility to PRRSV infection.

EXAMPLE 11

This example permits quantification of CD 151 levels in different swine breeding lines.
Materials and Methods
This Example is similar to Example 4 except that the plasmid pKSU is used for quantitative purposes. This plasmid contains full-length open reading frames of CD 151. A known amount of this plasmid (e.g. 0.05 micrograms) is introduced into the PCR tubes and known dilutions of the predetermined sample will be added to cover the range of the expected CD 151 levels in different swine tissues, thereby providing known prequantified standards. The amount of CD 151 in unknown swine samples will be quantified by comparison with the known standard curve. Additionally, to find the precise amount of CD 151 in swine tissues, a quantitative TaqMan for CD 151 can be performed. This will provide precise quantification of CD 151 in germplasm and peripheral blood platelets in picogram to nanogram amounts per milliliter or per gram of known swine tissue, per milliliter of germplasm, or per one million swine platelets or per one million swine spermatazoa.
Results By quantitative CD 151 RT-PCR, swine breeding lines lower in CD 151 will be selected for breeding for reduced PRRSV susceptibility.

EXAMPLE 12

This example illustrates the use of non-simian, recombinant cell lines for production of higher titer, safer swine vaccines to control or prevent PRRSV.
Materials and Methods Based on this invention, non-simian cell lines transformed with CD 151 are not only susceptible to PRRSV but propagate the PRRS virus to much higher titers than parent cell lines. First, the cell lines will be checked for contaminations such as Mycoplasma, porcine parvovirus, and BVD virus using methods that are well known in the art. Once the cell line has been found to be free of these contaminates, the cell line will be plated in flasks or roller bottles and will be infected with plaque purified PRRS virus. The American isolate, Lelystad virus, or any other PRRS virus isolate can be used. The cell cultures will be infected for sixty hours after which they will be frozen at −80° C., and freeze-thawed 3 times. Cellular material will be removed and clear supernatant will be used as a vaccine after titration. It is recommended to use 1 million PFUs/ml and the dose of the vaccine will be 1 ml intramuscularly in the presence of the parenteral adjuvants. This vaccine can even be diluted because of its high titer for making specific doses per vial. Alternatively, various combinations that are known in this field of art can be applied. All manipulations and modifications included in this invention are routine in the field of preparation of biologics for animal vaccines.
Results The preceding materials and methods produce a safe, high titer killed or modified-live virus vaccine for PRRSV in non-simian cell lines.

EXAMPLE 13

This example shows the application of non-simian cell lines for propagation of PRRSV for development of in vitro diagnostic assays.
Materials and Methods Advantageously, non-simian cell lines can be used for propagating PRRSV because of their higher susceptibility for propagating the wild type virus from clinical samples such as nasal swabs and tissues such as lung, lymph nodes, or pools of tissues from cases suspected of PRRSV, swine abortions, or respiratory diseases. These cells are plated till monolayers are confluent in approximately seventy-two hours, samples are inoculated, and the cell line is checked for the presence of virus by a fluorescent antibody test using SDOW 17 FITC conjugated antibody. The propagated virus, as produced in Example 12, is used to coat ELISA plates and the standard procedures for development of ELISA technology for detection of PRRSV antibodies have been described using the procedures of Witte et. al., Development of a Recombinant Nucleoprotein-Based Enzyme-Linked Immunosorbent Assay for Quantification of Antibodies against Porcine Reproductive and Respiratory Syndrome Virus, 7 *Clinical and Diagnostic Laboratory Immunology*, 700–702, (2000), the content and teachings of which are hereby incorporated by reference. Currently the ELISA test is considered as the gold-standard for monitoring the swine PRRSV antibodies.
Results The wild type PRRS virus can be detected in vitro by virus isolation. Additionally, the presence and quantity of PRRS antibodies can be detected using these immunodiagnostic assays. Other assays which would provide in vitro diagnostic tests for detecting wild type PRRS virus and antibodies and verifying PRRS diagnoses in swine herds include indirect fluorescent antibody tests and indirect immunoperoxidase tests. Such tests are well known in the art and could be developed using no more than ordinary skill.

EXAMPLE 14

This example shows the application of immunodiagnostic tools, (e.g. quantitative ELISA) for CD 151 which can be used to monitor swine fluid samples including platelet lysates, sperm lysates and swine alveolar macrophage lysates.
Materials and Methods Protein is detected quantitatively using the methods of Witte et. al., 2000. For example, the level of CD 151 in swine samples can be detected using these methods. Samples will be freeze-thawed. The level of protein will be monitored.
Results This example permits the mass screening of swine samples using a quantitative CD 151 ELISA. Additionally, the amount of CD 151 protein per ml of swine sample or per gram of tissue will be detectible using these methods.

EXAMPLE 15

This example illustrates that CD 151 from sources other than simian sources can be used to render a previously non-susceptible cell line susceptible to PRRSV infection.
Materials and Methods A sample of cellular material containing CD 151 is obtained from a swine. The RNA is extracted from this sample as previously described and then the porcine CD 151 is isolated using RT-PCR. The isolated CD 151 is then deposited in an appropriate mammalian expression vector which can be used to render previously non-susceptible cell lines susceptible to PRRSV infection. Examples of such cell lines include BHK-21. Additionally, by depositing the vector into previously susceptible cell lines, these cell lines can be used to overexpress the CD 151.
Results Previously non-susceptible cell lines are rendered susceptible to PRRSV infection after depositing a vector containing porcine CD 151 into the cell line. Previously susceptible cell lines can overexpress the inserted CD 151. Thus, CD 151 from any source can be used to transform cell lines including non-simian cell lines so that they express CD 151. This proves that, the source of the CD 151 (simian, porcine, etc.) is not relevant to practice the invention and that all aspects of the invention using simian CD 151 can also be accomplished using porcine or other similar CD 151 sequences.

EXAMPLE 16

This example proves that tetraspan CD 151 or its related homologues in other species such as equine CD 151 can be used to propagate the Arteriviruses from equine and other species.

Materials and Methods

A heterologous CD 151 sequence is isolated and used to make recombinant cell lines as previously described. This cell line is then used to isolate and propagate the virus as previously described.

Results

Similar to PRRSV, other Arteriviruses can be isolated and propagated to high titers in homologous and heterologous cell lines including non-simian cell lines. Thus, other Arteriviruses can be approached in the same manner as PRRSV in identifying methods of producing high titer vaccines in cell lines which were previously resistant to infection by the Arteriviruses and increasing virus production in cell lines which were previously susceptible to the Arteriviruses.

Discussion

Viruses are obligatory internal parasites that have limited genetic material for replication. Viruses often utilize host cellular factors, in the form of RNA binding proteins, transcription factors, proteases, and membrane factors for their replication. RNA binding proteins could play roles in transcription, translation, orientation, and transport of viral RNA. To understand how viral RNA replication proceeds, it is important to identify and characterize these proteins. There is no report of identification of host cellular proteins binding to the 3' UTR of PRRSV.

Here the identification of a novel 29 kD glycoprotein, simian CD 151, which binds to the 3'UTR of PRRSV is reported. CD 151 is a transmembrane glycoprotein, belonging to the tetraspan or transmembrane 4 superfamily of cellular proteins. Tetraspans have four highly conserved hydrophobic domains spanning the lipid bilayer and two extracellular domains. The N and C terminals are found in the cytoplasm. The simian CD 151 shares 98% homology with PETA-3, which is found mainly in endothelial cell membranes, platelets and megakaryocytes, epithelium, lung, muscle, Schwann cells, and glomeruli. This protein has been shown to be upregulated in human T cells transformed by T cell leukemia virus type 1 and has been named SFA-1. Significant amounts of PETA-3 are present in intracellular compartments, localized to perinuclear vesicles, accounting for 66% of the total amount of PETA-3 protein present in endothelial cells. Tetraspan CD 151 is required for the early step in metastasis of tumors and is involved in interactions with the integrins in hemopoietic cell lines, modulation of cell-cell adhesions, and transmembrane signaling through protein-protein interactions.

After demonstrating that CD 151 binds to the 3'UTR of PRRSV, the correlation between the presence of CD 151 and susceptibility to PRRSV infection was tested. It was found that MA 104, MARC, COS-7 and Vero cell lines which are all derived from kidney cells have CD 151. However, BHK-21 and MDBK cells are also derived from kidney cells, but they lack CD 151. Thus, CD 151 as a kidney specific protein is ruled out. The PRRSV does not enter BHK-21 cells, but the transfection of these cells with either the PRRSV RNA or the infectious cDNA clone results in productive viral infection without spreading to neighboring cells. Thus, it was reasoned that although BHK-21 cells support the replication of PRRSV RNA, they lack the cellular factors required for the entry of the virus or viral RNA. Since it was found that CD 151 is a transmembrane protein, it was reasoned that it might have a role in entry of PRRSV and/or viral RNA. There is a previous report that CD 9, another tetraspan, renders MDBK anon-susceptible cell line, susceptible to canine distemper virus infection and functions as an entry molecule. To prove that CD 151 is one of the susceptibility factors of PRRSV infection, it was determined that BHK-21 cells expressing CD 151 get infected by PRRSV while the parent cell line lacking CD 151 did not get infected. Thus, because CD 151 is a transmembrane molecule, it might play a role in virus entry or viral RNA entry into BHK-21 cells.

Figure 9:
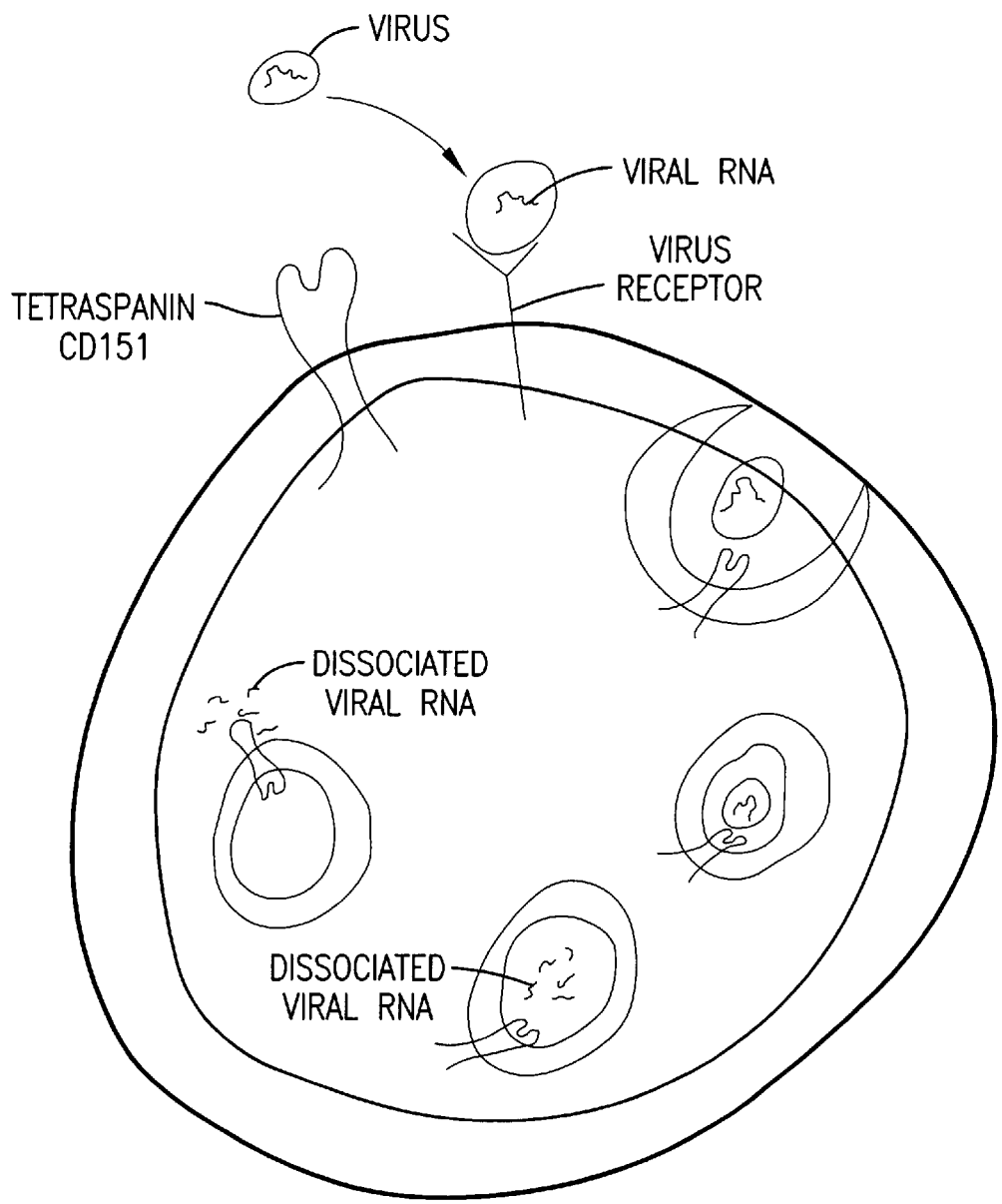
FIG. 9 is a schematic representation of the mechanism of PRRS viral RNA entry into a target cell and the role of RNA-binding proteins such as CD 151.

Entry of the virus into cells occurs by the interaction of viral proteins with specific viral receptors present on the cell membrane. These receptors are very important determinants of susceptibility to viral infection. Previous studies have demonstrated that PRRSV binds to a heparin-like molecule, and entry of the virus occurs by receptor-mediated endocytosis. Low pH in these vesicles is essential for the productive infection. Coimmunoprecipitation was performed to determine if there is any interaction between PRRSV proteins and CD 151, however, there was no evidence for direct protein-protein interaction between them. This is in agreement to the previous observation that CD 9, another tetraspan is a susceptibility factor for canine distemper but it does not directly interact with the viral proteins. For a protein to be a receptor, it has to interact with the viral proteins; thus, the CD 151 does not function as the receptor. Because CD 151 is present in the vesicles and also in the membranes, its role as an RNA transporter molecule is predicted based on two observations: first, it rendered non-susceptible BHK-21 cells susceptible to viral infection and secondly, MARC cells that overexpress CD 151 (by stable transfection) exhibit a 100-fold increase in virus production as compared to the native cell line. This effect of CD 151 on viral replication may be explained by increased cellular uptake of the viral RNA during the entry of the virus with CD 151 functioning as an RNA-transport molecule. This process is shown schematically in FIG. 9. There are previous data where the RNA binding proteins are predicted to function as RNA transporter molecules. Testis/brain RNA binding protein interacts with the 3'UTR of the mRNA and it transports mRNA to specific intracellular sites where they are translated. This protein is also reported to transport the mRNAs between cells. In tobacco mosaic virus, a 30 kD movement protein is involved in transport of the viral RNA from cell to cell via the plasmodesmata. In beet necrotic yellow virus, proteins p 42, p 14, and p 13 are involved in the movement of viral RNA through the plasmodesmata by interaction with the viral RNA. There is no report of an RNA transport molecule in animal viruses. In PRRSV infection, the CD 151 either alone or in conjugation with other proteins might act as the RNA transporter molecule for entry into the cytoplasm after the virus uncoats in the vesicles. Thus, the present invention demonstrates that CD 151 is involved in the replication of PRRS virus mainly as a viral RNA entry molecule.

To determine whether the CD 151 transmembrane protein plays a role in entry of the virus/viral RNA into the cell, BHK-21 cells were chosen for testing because BHK-21 cells are resistant to PRRSV infection. However, when BHK-21 cells are transfected with either the viral RNA or the infectious cDNA clone of PRRSV, they support the replication of the virus. Thus the resistance factor in BHK-21 cells might be associated with the entry molecule. The fact that BHK-21 cells lack CD 151 was definitively shown by RT-PCR (FIG. 5, lane 6) using CD 151 specific primers. BHK-21 cells expressing CD 151 were obtained by stable transfection as described above in the Materials and Methods. These transfected cells were infected with PRRSV and tested for virus production by immunohistochemistry. Notably, it was found that the CD 151 transfected cells became infected with PRRSV but the parent BHK-21 cells lacking CD 151 (verified in FIG. 6) did not become infected.

Another advantageous aspect of the present invention is that the baby hamster kidney (BHK) cell line used in these experiments is not of simian origin. Thus it differs from all other cell lines used for propagating PRRSV which are of simian origin. This provides a great advantage because the use of non-simian cells lines poses no risk of transmission of primate or simian viruses to pigs, especially xenotransplanted pigs. By using non-simian cell lines to propagate PRRSV, primate and/or simian viruses will not be introduced into swine populations and will therefore not pose a risk to the human population. Also, because these cells expressing CD 151 have higher titers of PRRSV, they are more convenient and economically useful for propagating PRRSV for vaccine production. Advantageously, these cells can be used to make killed and live PRRS virus vaccines and serodiagnostic assays.

We claim:

1. A method of selecting swine for breeding comprising the steps of:
   screening a sample of cellular material from said swine for the presence of CD 151 protein to obtain a CD 151 level;
   comparing said CD 151 level with a known standard related to CD 151 levels;
   and selecting swine for breeding which have a CD 151 level lower than said known standard.

2. The method of claim 1, said sample being of known origin.

3. The method of claim 1, said sample being of the same origin as said known standard.

4. The method of claim 1, said CD 151 level being at least about 20% lower than said known standard.

5. The method of claim 4, said CD 151 level being at least about 35% lower than said known standard.

6. The method of claim 5, said CD 151 level being at least about 50% lower than said known standard.

7. The method of claim 1, said sample being selected from the group consisting of blood, semen, ova, germplasm, and sperm cells.

8. A method of selecting swine for breeding based on the amount of a transmembrane glycoprotein present in a sample of the swine's cellular material, said method comprising the steps of:
   selecting CD 151 as said transmembrane glycoprotein;
   assaying a sample of the swine's cellular material to determine the amount of CD 151 present therein;
   using the results of said assay to select swine for breeding.

9. The method of claim 8, said method further comprising the step of comparing the determined amount of CD 151 with a known standard for CD 151 amounts.

10. The method of claim 9, further including the step of selecting animals for breeding wherein the selected animals have CD 151 amounts lower than the known standard amounts.

11. The method of claim 8, said cellular material being from a known source.

12. The method of claim 9, said cellular material and said known standard being from the same type of cellular source.

* * * * *

SEQUENCE LISTING

```
<160> NUMBER OF SEQ ID NOS: 7

<210> SEQ ID NO 1
<211> LENGTH: 1466
<212> TYPE: DNA
<213> ORGANISM: Simian Gen. Sp.
<220> FEATURE:
<221> NAME/KEY: misc_feature
<222> LOCATION: (451)..(451)
<223> OTHER INFORMATION: n is a, c, g or t
<220> FEATURE:
<221> NAME/KEY: misc_feature
<222> LOCATION: (484)..(484)
<223> OTHER INFORMATION: n is a, c, g or t
<220> FEATURE:
<221> NAME/KEY: misc_feature
<222> LOCATION: (556)..(556)
<223> OTHER INFORMATION: n is a, c, g or t
<220> FEATURE:
<221> NAME/KEY: misc_feature
<222> LOCATION: (616)..(616)
<223> OTHER INFORMATION: n is a, c, g or t
<220> FEATURE:
<221> NAME/KEY: misc_feature
<222> LOCATION: (645)..(645)
<223> OTHER INFORMATION: n is a, c, g or t
<220> FEATURE:
<221> NAME/KEY: misc_feature
<222> LOCATION: (649)..(649)
<223> OTHER INFORMATION: n is a, c, g or t
<220> FEATURE:
<221> NAME/KEY: misc_feature
<222> LOCATION: (652)..(652)
<223> OTHER INFORMATION: n is a, c, g or t
<220> FEATURE:
<221> NAME/KEY: misc_feature
<222> LOCATION: (655)..(655)
<223> OTHER INFORMATION: n is a, c, g or t
<220> FEATURE:
<221> NAME/KEY: misc_feature
<222> LOCATION: (884)..(884)
<223> OTHER INFORMATION: n is a, c, g or t
<220> FEATURE:
<221> NAME/KEY: misc_feature
<222> LOCATION: (903)..(903)
<223> OTHER INFORMATION: n is a, c, g or t
<220> FEATURE:
<221> NAME/KEY: misc_feature
<222> LOCATION: (917)..(917)
<223> OTHER INFORMATION: n is a, c, g or t
<220> FEATURE:
<221> NAME/KEY: misc_feature
<222> LOCATION: (1194)..(1194)
<223> OTHER INFORMATION: n is a, c, g or t
```

-continued

<400> SEQUENCE: 1

```
gtcccggact ccgacgagtg gtagccccag gatgggtgag tttaacgaga agaagacaac    60
atgtggcacc gtttgcctca agtacctgct gtttacctac aactgctgct tctggctggc   120
cggcctggct gtcatggcag tgggcatctg gacgctggcc ctcaagagtg actacatcag   180
cctcctggcc tcgggcacct acctggccac agcctacatc ctggtggtgg cgggcgctgt   240
cgtcatggtg accggggtct tgggctgctg tgccaccttc aaggagcgtc ggaacctgct   300
gcgcctgtac ttcatcctgc tcctcatcat ctttctgctg gagatcatcg ctggtgtcct   360
cgcctatgtc tactaccagc agctgaacac agagctcaag gagaacctta aggacaccat   420
ggccaagcgc taccaccagc cgggtcacga ngccgtgacc agcgctgtgg accaactgca   480
gcangagttc cactgctgtg gcagcaacaa ctcacaggac tggcgggaca gtgaagtgga   540
tccgcttaag ggaagnccgt ggccgcgtgg tccccgatag ctgcttgcaa gacggtggtg   600
gctggttgtg ggcaancggg accacgcctt caacatttac aaggnggang nggnttcat   660
caccaagttg gagaccttca tccaggagca cctcagggtc attggggctg tggggactgg   720
cattgcctgt gtgcaggtct ttggcatgat cttcacatgc tgcctgtaca ggagcctcaa   780
gctggagcac tactgaccct gccctgggct tggccgcggc tctgtgcttt gctgctgctg   840
cacccaacta ctgagctgag accactgagt accaggggct gggntccctg atgacaccca   900
ccntgtgcca tcaccanaac tttggggacc ccaaccccag aggcaagctt caagtgcctt   960
tcgctgcaca ccaaagccca gcagggaagt gagggggct ggcgggacga cggtatcggg  1020
ggtgttttgt ggggctgcct gaacacattc tgcctggtgg tcagatgcag gctagccggg  1080
gccttgctga gtagggcaag gccgagtgtt cccagcaggg ggagaagccc ttcacatccc  1140
aggcccttca gggattaggg ctttgccttg cagccacatg gccccatccc agtntgagaa  1200
gctgagtaag ctctgaccct tgggcctggg cctctgcccc tccccaccca ggcctcgtct  1260
ccctcagagc ccctgctgtc ttccccaccg cagtcaccac cacccgaaat gccacatggt  1320
cacttgtgca ctgccccgtc catgtgcctg tgtggggcag gggcctcccg gttttgttca  1380
ctgctgtacc cagatgccta caaccatccc tgccacatac aggtgctcaa taaacacttg  1440
tggggcagat ggacgaaaaa aaaaaa                                       1466
```

<210> SEQ ID NO 2
<211> LENGTH: 22
<212> TYPE: DNA
<213> ORGANISM: Artificial
<220> FEATURE:
<223> OTHER INFORMATION: This is a forward primer sequence.

<400> SEQUENCE: 2

```
ccccattttc ctctagcgac tg                                             22
```

<210> SEQ ID NO 3
<211> LENGTH: 22
<212> TYPE: DNA
<213> ORGANISM: Artificial
<220> FEATURE:
<223> OTHER INFORMATION: This is a reverse primer.

<400> SEQUENCE: 3

```
cggccgcatg gttctcgcca at                                             22
```

<210> SEQ ID NO 4

-continued

```
<211> LENGTH: 20
<212> TYPE: DNA
<213> ORGANISM: Artificial
<220> FEATURE:
<223> OTHER INFORMATION: This is a forward primer.

<400> SEQUENCE: 4
tgggctggca ttcttgaggc                                               20

<210> SEQ ID NO 5
<211> LENGTH: 21
<212> TYPE: DNA
<213> ORGANISM: Artificial
<220> FEATURE:
<223> OTHER INFORMATION: This is a reverse primer

<400> SEQUENCE: 5
ttcgggccgc atggttctcg c                                             21

<210> SEQ ID NO 6
<211> LENGTH: 20
<212> TYPE: DNA
<213> ORGANISM: ARTIFICIAL
<220> FEATURE:
<223> OTHER INFORMATION: This is a primer sequence.

<400> SEQUENCE: 6
cctacctggc cacagcctac                                               20

<210> SEQ ID NO 7
<211> LENGTH: 20
<212> TYPE: DNA
<213> ORGANISM: ARTIFICIAL
<220> FEATURE:
<223> OTHER INFORMATION: This is a reverse primer.

<400> SEQUENCE: 7
acaggcgcag caggttccga                                               20
```